US007435443B2

(12) United States Patent
Jiang

(10) Patent No.: US 7,435,443 B2
(45) Date of Patent: Oct. 14, 2008

(54) METHOD TO PREVENT LOW TEMPERATURE DEGRADATION OF ZIRCONIA

(75) Inventor: Guangqiang Jiang, Santa Clarita, CA (US)

(73) Assignee: Alfred E. Mann Foundation for Scientific Research, Santa Clarita, CA (US)

( * ) Notice: Subject to any disclaimer, the term of this patent is extended or adjusted under 35 U.S.C. 154(b) by 505 days.

(21) Appl. No.: 11/297,075

(22) Filed: Dec. 8, 2005

(65) Prior Publication Data

US 2006/0121206 A1 Jun. 8, 2006

Related U.S. Application Data

(62) Division of application No. 10/711,154, filed on Aug. 27, 2004, now Pat. No. 7,297,420.

(51) Int. Cl.

| | |
|---|---|
| ***B05D 5/00*** | (2006.01) |
| ***A61L 27/50*** | (2006.01) |
| ***A61L 27/10*** | (2006.01) |
| ***A61L 27/30*** | (2006.01) |

(52) U.S. Cl. ....................... 427/2.1; 427/2.24; 427/529; 427/530

(58) Field of Classification Search ....................... None
See application file for complete search history.

(56) References Cited

U.S. PATENT DOCUMENTS

| | | | | |
|---|---|---|---|---|
| 6,043,437 | A * | 3/2000 | Schulman et al. | 174/258 |
| 6,869,701 | B1 * | 3/2005 | Aita et al. | 428/698 |
| 7,037,603 | B2 * | 5/2006 | Lasater | 428/701 |
| 7,097,775 | B2 * | 8/2006 | Greenberg et al. | 216/2 |
| 2002/0120296 | A1 * | 8/2002 | Mech et al. | 607/2 |
| 2002/0172838 | A1 * | 11/2002 | Rigney et al. | 428/633 |
| 2003/0080085 | A1 * | 5/2003 | Greenberg et al. | 216/20 |
| 2006/0173497 | A1 * | 8/2006 | Mech et al. | 607/2 |
| 2008/0051862 | A1 * | 2/2008 | Mech et al. | 607/116 |
| 2008/0131611 | A1 * | 6/2008 | Hass et al. | 427/450 |

* cited by examiner

*Primary Examiner*—Marianne L Padgett
(74) *Attorney, Agent, or Firm*—Gary D. Schnittgrund

(57) ABSTRACT

The invention is directed to a method of producing the material that is unaffected by the low-temperature degradation, humidity-enhanced phase transformation typical of yttria-stabilized zirconia, as well as of yttria-stabilized tetragonal zirconia polycrystalline ceramic (Y-TZP). Because of the high fracture toughness and high mechanical strength, this class of materials is widely used, including as implants, such as for the packaging material for small implantable neural-muscular sensors and stimulators. The destructive phase transformation rate is dramatically reduced by coating the surface of the Y-TZP component with dense alumina by a physical vapor deposition process, preferably ion beam assisted deposition.

7 Claims, 1 Drawing Sheet

METHOD TO PREVENT LOW TEMPERATURE DEGRADATION OF ZIRCONIA

CROSS REFERENCE TO RELATED APPLICATION

This application is a divisional of U.S. patent application Ser. No. 10/711,154, filed Aug. 27, 2004, now U.S. Pat. No. 7,297,420.

FIELD OF THE INVENTION

This invention relates to a coating material and a method of increasing the useful life of an yttria-stabilized zirconia structure when implanted in living tissue.

BACKGROUND OF THE INVENTION

One widely employed bioceramic is alumina, which is considered bioinert. The search for an ideal bioceramic has included alumina, hydroxyapatite, calcium phosphate, and other ceramics. The first use of aluminas for implants in orthopedics and dentistry was in the 1960's. They were later employed in hip prostheses as early as 1970. Since those early days the quality and performance of aluminas have improved. High-purity, high-density, fine-grained aluminas are currently used for a wide range of medical applications, e.g. dental implants, middle ear implants, and hip or knee prostheses.

Although the aluminas currently available perform satisfactorily, a further improvement in strength and toughness would increase the safety factor and may extend usage to higher stressed components. A proposed candidate to add to this list is stabilized-zirconia, because of its potential advantages over alumina of a lower Young's modulus, higher strength, and higher fracture toughness. Another advantage of stabilized-zirconia is low-wear residue and low coefficient of friction. Because, zirconia undergoes a destructive phase change at between 1000° and 1100° C., changing from monoclinic to tetragonal, phase stabilization admixtures of calcia, magnesia, ceria, yttria, or the like are required.

Tetragonal zirconia polycrystalline ceramic, commonly known as Y-TZP, which typically contains 3 mole percent yttria, coupled with a small grain size, results in the metastable tetragonal state at room temperature. Under the action of a stress field in the vicinity of a crack, the metastable particles transform, accompanied by a 3% to 4% volume increase, by a shear-type reaction, to the monoclinic phase. Crack propagation is retarded by the transforming particles at the crack tip and by the compressive back stress on the crack walls behind the tip, due to volume expansion associated with transformation to the monoclinic phase.

The well-known transformation toughening mechanism is operative in zirconia ceramics whose composition and production are optimized such that most of the grains have the tetragonal crystal structure. These Y-TZP ceramics, most notably their mechanical properties in air at room temperature, are superior to those of zirconia-toughened aluminas and to other classes of zirconias. While the biocompatibility of Y-TZP ceramic has not been fully assessed, it has been preliminarily investigated.

For example, in one study by Thompson and Rawlings [see I. Thompson and R. D. Rawlings, "Mechanical Behavior of Zirconia and Zirconia-Toughened Alumina in a Simulated Body Environment," Biomaterials, 11 [7] 505-08 (1990)]. The result was that Y-TZP demonstrated a significant strength decrement when aged for long periods in Ringer's solution and was therefore unsuitable as implant material.

Drummond [see J. L. Drummond, J. Amer. Ceram. Soc., 72 [4] 675-76 (1989)] reported that yttria-stabilized zirconia demonstrated low-temperature degradation at 37° C. with a significant decrement in strength in as short a period as 140 to 302 days in deionized water, saline, or Ringers solution. He also reports on similar observation by others, where yttria-stabilized zirconia demonstrated a strength decrement in water vapor, room temperature water, Ringers solution, hot water, boiling water, and post-in vivo aging.

Y-TZP components suffer a decrement in strength properties after exposure for only a few days to humid environments. This degradation of mechanical properties occurs when moisture is present in any form, for example, as humidity or as a soaking solution for the Y-TZP component. Y-TZP components have been observed to spontaneously fall apart after times as short as a few weeks in room temperature water. This is of particular importance in living-tissue implanted devices that contain components made of this class of material. Long-term implantation of devices that contain yttria-stabilized (or partially-stabilized) zirconia components is not feasible with available materials.

One approach to preventing the low-temperature degradation of zirconia that was doped with 3 mole percent yttria is presented by Chung, et al. [see T. Chung, H. Song, G. Kim, and D. Kim, "Microstructure and Phase Stability of Yttria-Doped Tetragonal Zirconia Polycrystals Heat Treated in Nitrogen Atmosphere," J. Am. Ceram. Soc., 80 [10] 2607-12 (1997).]. The Y-TZP sintered material was held for 2 hours at 1600° or 1700° C. in flowing nitrogen gas.

Another approach to preventing low temperature degradation of zirconia in biomedical implants is disclosed by Lasater in U.S. application Ser. No. 10/853,922, now U.S. Pat. No. 7,037,603, while Jiang, et al., U.S. patent application Ser. No. 10/629,291, disclose a method of overcoming the pest low-temperature degradation in yttria-stabilized zirconia.

Analysis showed that the resulting surface consisted of cubic grains with tetragonal precipitates, while the interior was only slightly affected by the nitrogen exposure. Chung reported that low-temperature degradation was prevented because degradation of Y-TZP started at the surface, which is protected from degradation by the stable cubic phase.

Koh, et. al investigated an encapsulating layer deposited on the surface of tetragonal zirconia polycrystals to prevent the low-temperature degradation of zirconia that was doped with 3 mole percent yttria [see Young-Hag Koh, Young-Min Kong, Sona Kim and Hyoun-Ee Kim, "Improved Low-temperature Environmental Degradation of Yttria-Stabilized tetragonal Zirconia Polycrystals by Surface Encapsulation", J. Am. Ceram. Soc, 82 [6] 1456-58 (1999)]. The layer, composed of silica and zircon, was formed on the surface by exposing the zirconia specimens next to a bed of silicon carbide powder in a flowing hydrogen atmosphere that contained about 0.1% water vapor at 1450° C.

An alternate material and an easy to apply method of producing stable material to prevent the detrimental low-temperature phase change are needed.

DETAILED DESCRIPTION OF THE PREFERRED EMBODIMENT

A broadly applicable material and method of producing the material begins with the densified as-sintered, tetragonal zirconia polycrystalline ceramic (Y-TZP) material that is produced by processes that are known to those skilled in the art, containing about 3 mole percent of yttria.

Figure 1:
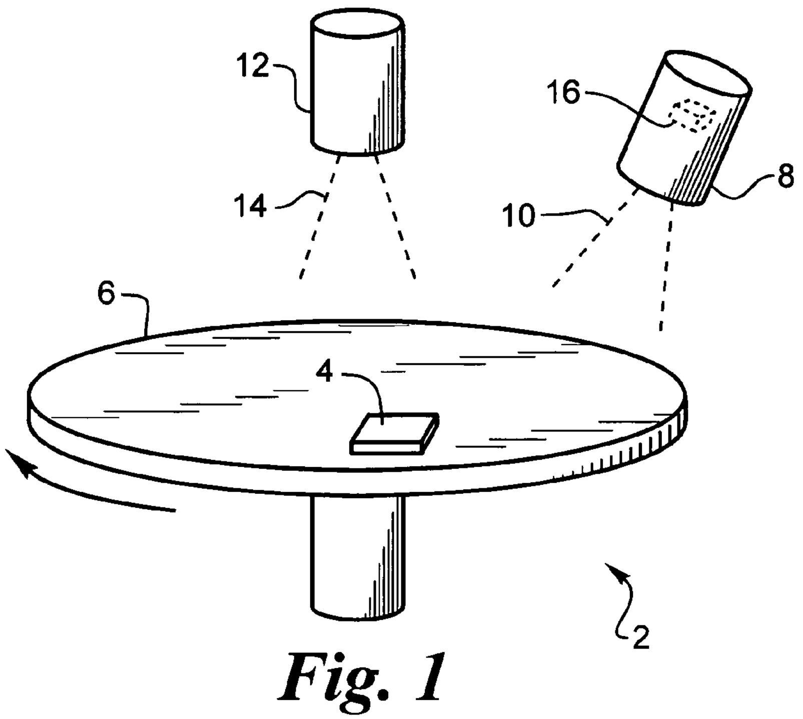
FIG. 1 presents a schematic representation of an ion beam assisted deposition apparatus.

The Y-TZP material is formed into a desired final shape and is then coated with alumina by the ion beam assisted deposition (IBAD) process of FIG. 1. The IBAD process creates a conformal coating, versus a line-of-sight coating, of alumina. The resulting alumina coating is dense and strongly adherent to the Y-TZP substrate 4. Unexpectedly, this coating has been shown to prevent or minimize the destructive low-temperature degradation of Y-TZP ceramic that occurs in moist environments. Alternate deposition methods are known, including magnetron sputter deposition and ion implantation coating deposition, however neither has been investigated for alumina on Y-TZP.

In a preferred embodiment, the coating thickness is at least about 1.6 microns. If the coating is less than about 1.6 microns thick then it is more likely to allow low temperature degradation of the Y-TZP ceramic, while if the coating thickness is greater than about 10 microns, then the coating is more likely to crack or spall off of the substrate. The average grain size of the alumina is preferably less than about 0.5 micron average, as measured by the line intersection method. This increases the toughness of the coating.

The IBAD process apparatus 2, FIG. 1, involves placing a substrate 4, which is also often referred to as the "target", to be coated on a substrate holder 6. The substrate is heated to about 300° C. The substrate holder 6 preferably rotates slowly at about one revolution per minute, to assist in obtaining a uniformly thick and dense coating on substrate 4. An ion gun 8, substrate holder 6, and e-beam evaporator 12 are located near the substrate in an environmentally controlled chamber, which is preferably a vacuum chamber that allows an inert gas, preferably argon, to be backfilled into the chamber with a small amount of oxygen. In alternate embodiments, other inert gases, such as nitrogen, or mixtures of inert gases may be utilized in combination with oxygen. In a preferred embodiment, there are two sources of argon; one to the ion gun and one to the IBAD chamber.

The ion gun 8 includes a source of the desired coating, preferably an alumina source 16, in a preferred embodiment. An ion beam 10 is generated wherein the energetic ions of alumina are directed toward the substrate 4. Simultaneously and continuously with the release of the ions, the e-beam evaporator 12 bombards the substrate 4 and the alumina coating, as it is forming, with an electron beam 14 that is emitted by a heated tungsten filament. It is preferred that the alumina coating be comprised of alpha-alumina or amorphous alumina. Because alpha-alumina is stronger, harder, and has a higher specific gravity than other aluminas, including amorphous alumina, alpha-alumina is a preferred phase. Amorphous alumina may be converted to alpha-alumina by annealing at about 1000° C. The IBAD process yields both amorphous alumina and alpha alumina in proportions that are dictated by the deposition parameters. A blend of alpha-alumina and amorphous alumina results under certain deposition parameters. It is believed that rapid quenching of the vapor phase results in a predominance of amorphous alumina. Therefore, control of the deposition parameters allows the preferred alpha-alumina phase to be formed in the coating on substrate 4.

It is known to those skilled in the art that the resulting coating has a high bulk density, comprising very low open or closed porosity, preferably less than 1.0% total porosity. Therefore, the alumina coating offers excellent resistance to moisture penetration, thereby eliminating or dramatically reducing moisture penetration and diffusion to the substrate 4.

EXAMPLE

The base vacuum level is about $1\times10^{-7}$ Torr and the working pressure of argon plus oxygen is about $3\times10^{-4}$ Torr. In a chamber of approximately one gallon in volume, the flow rates to the ion gun 8 of the argon-oxygen mixture about 10 scc/m argon plus 5.5 scc/m oxygen. The flow rates to the IBAD chamber are about 5.5 scc/m oxygen and about 3.5 scc/m of argon.

The substrate temperature is about 300° C. The electron beam evaporation source is a solid, dense block of single crystal sapphire alumina with a purity of at least about 99.99 atomic percent.

The deposition rate is about 1.5 angstroms per second at an ion beam bombardment energy of about 1000 eV and an ion beam current of about 26 mA. In alternate embodiments, the film is bombarded with ions from an ion gun with energies typically in the range of 1.0 to 1.5 Kev. As a result, energy is transferred to the coating atoms, allowing them to migrate on the surface, and the coating can grow in a more uniform manner.

A 1.6 micron thick alumina coating was applied by IBAD on a sealed ceramic case comprised of Y-TZP. X-ray diffraction analysis was performed on this unit prior to and after soaking in 127° C. steam for 20, 85, 137, and 201 hours. The X-rays penetrate the thin alumina layer and allow peak detection of 2 Theta angles of 28.2, 30.2 and 31.3 degrees. The monoclinic phase fraction is calculated by the modified Garvie-Nicholson equation. As presented in FIG. 2, the monoclinic phase percentage changes with the increase in soak time. Initially the phase transformation rate of the ceramic coated with 1.6 microns alumina is much slower than that of a ceramic having no alumina coating. After 150 hours, the monoclinic phase increased abruptly. The alumina coated ceramic self-destructed after 201 hours of soaking, when the monoclinic phase was 49%, which is less than the 70% monoclinic saturation level.

Figure 2:
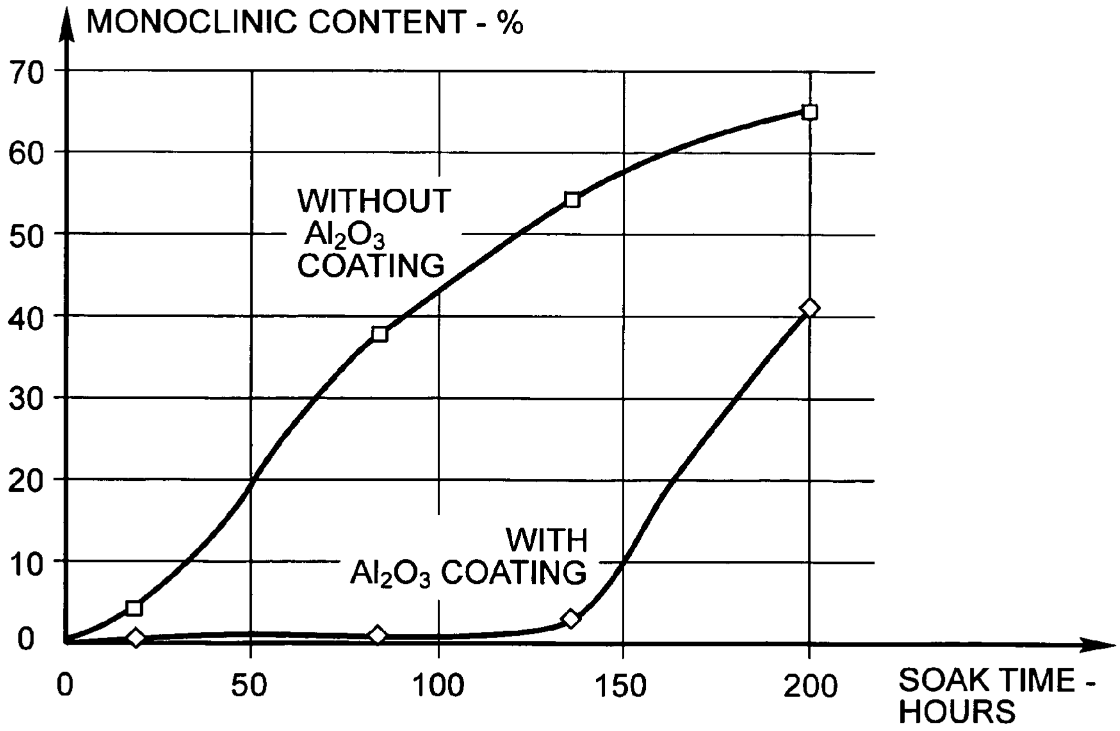
FIG. 2 presents a chart of the effect of the alumina coating on monoclinic phase increase with aging time.

FIG. 2 presents the destructive phase conversion of tetragonal to monoclinic phase when Y-TZP ceramic that has been left in the as-formed condition (i.e., uncoated) and Y-TZP ceramic that has been coated by the IBAD process with a thin alumina film are exposed to 127° C. steam in a static, unstressed state. This accelerated life test, which equates 100 hours of soak time with an implant service life of 5.84 years, is disclosed by Jiang, et al. in U.S. patent application Ser. No. 10/651,462 now U.S. Pat. No. 6,997,701.

Obviously, many modifications and variations of the present invention are possible in light of the above teachings. It is therefore to be understood that, within the scope of the appended claims, the invention may be practiced otherwise than as specifically described.

What is claimed is:

1. A method of manufacturing a degradation resistant component for use in living tissue, comprising the steps of:

providing a component comprised of yttria-stabilized tetragonal zirconia polycrystal ceramic;

depositing a coating of alumina by ion beam assisted deposition on the component; and selecting deposition parameters to achieve a coating comprised of less than about 1.0 percent total porosity.

2. The method according to claim 1, wherein said depositing a coating comprises the step of depositing alpha-alumina, amorphous alumina, or a blend thereof.

3. The method according to claim 1, wherein said depositing a coating comprises the step of depositing a coating comprised of an average grain size less than about 0.5 microns.

4. The method according to claim 1, wherein said depositing a coating of alumina comprises depositing a coating comprising a thickness that is greater than about 1.6 micron and less than about 10 microns.

5. The method according to claim 1, wherein said providing a component comprises providing a component comprising about 3 mole percent yttria.

6. The method according to claim 1, wherein said selecting deposition parameters comprises selecting an ion beam bombardment energy of about 1000 eV and an ion beam current of about 26 mA.

7. The method according to claim 1, wherein said depositing a coating comprises depositing at a rate of about 1.5 angstroms per second.

* * * * *